United States Patent
Jaspers

(10) Patent No.: US 9,060,792 B2
(45) Date of Patent: Jun. 23, 2015

(54) MANIPULATOR FOR AN INSTRUMENT FOR MINIMALLY INVASIVE SURGERY, AND A POSITIONING AID FOR POSITIONING SUCH AN INSTRUMENT

(75) Inventor: Joris Jaspers, Utrecht (NL)

(73) Assignee: Academisch Medisch Centrum van de Universiteit van Amsterdam, Amsterdam (NL)

( * ) Notice: Subject to any disclaimer, the term of this patent is extended or adjusted under 35 U.S.C. 154(b) by 841 days.

(21) Appl. No.: 12/604,839

(22) Filed: Oct. 23, 2009

(65) Prior Publication Data
US 2010/0121347 A1    May 13, 2010

Related U.S. Application Data

(63) Continuation-in-part of application No. PCT/NL2008/050230, filed on Apr. 21, 2008.

(30) Foreign Application Priority Data

Apr. 24, 2007  (NL) .................................... 2000607

(51) Int. Cl.
*A61B 19/00* (2006.01)
*A61B 17/00* (2006.01)
*A61B 17/29* (2006.01)

(52) U.S. Cl.
CPC ....... *A61B 19/22* (2013.01); *A61B 2017/00477* (2013.01); *A61B 2017/291* (2013.01); *A61B 2019/2242* (2013.01); *A61B 2019/2265* (2013.01)

(58) Field of Classification Search
CPC .... A61B 19/201; A61B 19/22; A61B 17/062; B25J 11/00; B25J 9/00
USPC ............. 606/130, 205, 209, 1; 414/1, 729; 135/126, 128; 211/41.5, 41.6, 85, 211/126.6, 130.1; 248/346.3, 167, 136, 248/150, 162.1, 280.11, 292.11, 297.11; 901/14, 15, 48
See application file for complete search history.

(56) References Cited

U.S. PATENT DOCUMENTS

| 2,774,488 | A |   | 12/1956 | Goertz et al. |
| 4,756,655 | A |   | 7/1988 | Jameson |
| 5,397,323 | A |   | 3/1995 | Taylor et al. |
| 5,697,939 | A | * | 12/1997 | Kubota et al. ................. 606/130 |
| 5,825,536 | A | * | 10/1998 | Yasunaga et al. ............. 359/384 |

(Continued)

FOREIGN PATENT DOCUMENTS

| DE | 102005031494 | 1/2007 |
| WO | WO 99/26167 | 11/1994 |

(Continued)

*Primary Examiner* — Darwin Erezo
*Assistant Examiner* — Richard Louis
(74) *Attorney, Agent, or Firm* — Peacock Myers, P.C.; Jeffrey D. Myers

(57) ABSTRACT

A manipulator for an instrument for minimally invasive surgery, having at a proximal end a handle for operating the instrument, and wherein the instrument is removably placed at a distal end, and wherein a parallelogram construction is provided between the proximal end and the distal end for guaranteeing an unambiguous positional relationship between the handle and the instrument, wherein the parallelogram construction is coupled with a system of bars for controlling the position of the parallelogram construction, the bars of the system of bars being connected to the parallelogram construction as well as to each other by means of cardan joints.

6 Claims, 11 Drawing Sheets

(56) References Cited

U.S. PATENT DOCUMENTS

Figure 1:
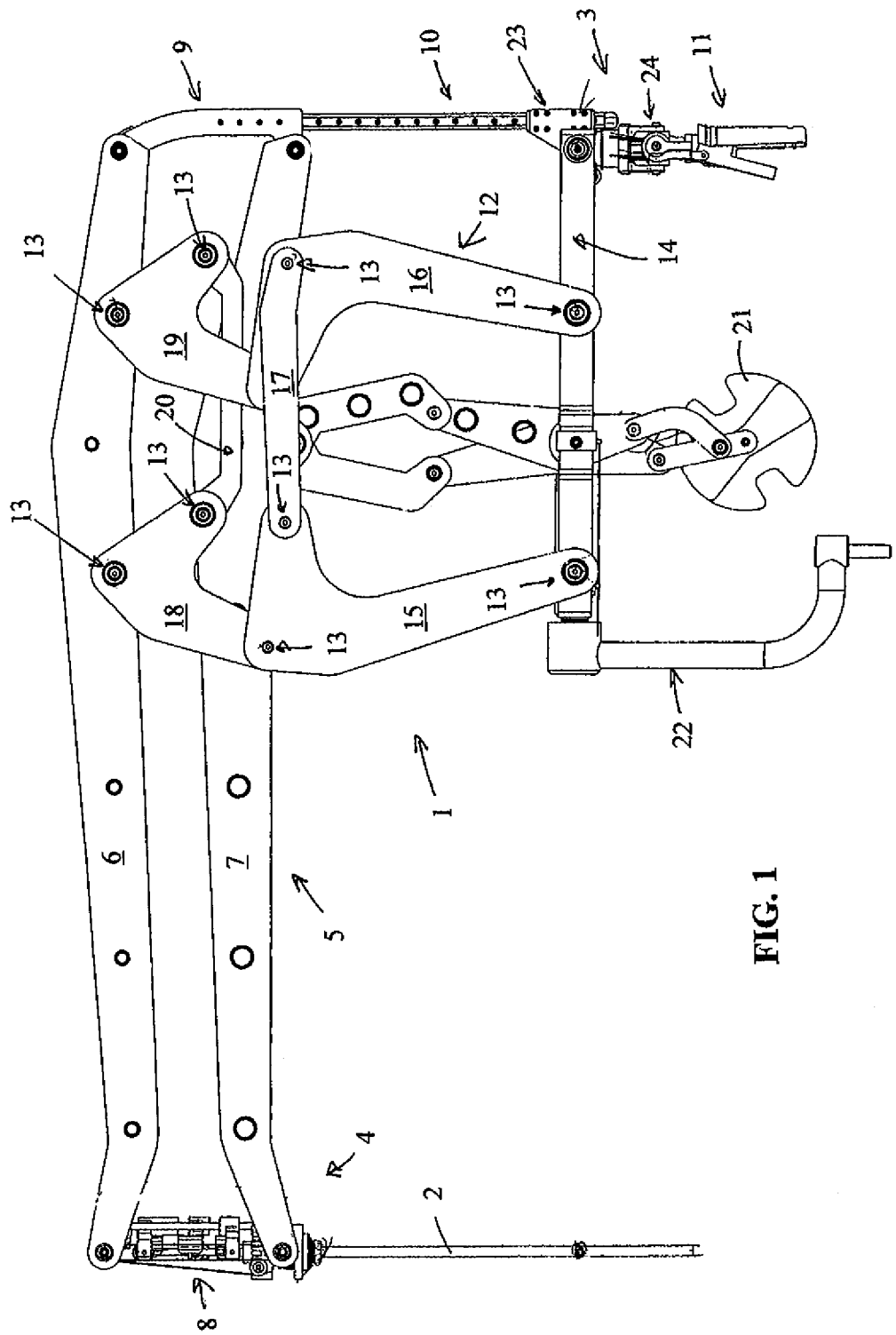

| | | | |
|---|---|---|---|
| 5,876,325 A | 3/1999 | Mizuno et al. | |
| 6,026,701 A | 2/2000 | Reboulet | |
| 6,095,011 A * | 8/2000 | Brogårdh | 74/490.03 |
| 6,554,844 B2 * | 4/2003 | Lee et al. | 606/130 |
| 6,665,554 B1 | 12/2003 | Charles et al. | |
| 6,702,805 B1 * | 3/2004 | Stuart | 606/1 |
| 6,723,106 B1 | 4/2004 | Charles et al. | |
| 6,936,042 B2 | 8/2005 | Wallace et al. | |
| 2003/0197482 A1 * | 10/2003 | Osuka et al. | 318/568.21 |
| 2004/0091348 A1 * | 5/2004 | Kong et al. | 414/735 |
| 2004/0138524 A1 | 7/2004 | Ueda et al. | |
| 2005/0058929 A1 | 3/2005 | Kennedy et al. | |
| 2005/0119641 A1 | 6/2005 | Jaspers | |
| 2006/0214095 A1 * | 9/2006 | Nagasawa et al. | 250/234 |
| 2007/0156122 A1 * | 7/2007 | Cooper | 606/1 |

FOREIGN PATENT DOCUMENTS

| | | |
|---|---|---|
| WO | WO 96/39944 | 12/1996 |
| WO | WO 99/50721 | 10/1999 |
| WO | WO-0028882 | 5/2000 |
| WO | WO-03086219 | 10/2003 |
| WO | WO-2004037103 | 5/2004 |

\* cited by examiner

MANIPULATOR FOR AN INSTRUMENT FOR MINIMALLY INVASIVE SURGERY, AND A POSITIONING AID FOR POSITIONING SUCH AN INSTRUMENT

This application is a continuation-in-part application of international Patent Application Ser. No. PCT/NL2008/050230, entitled "Manipulator for an Instrument for Minimally Invasive Surgery, and a Positioning Aid for Positioning Such an Instrument", by Joris Jaspers, to Academisch Medisch Centrum van de Universiteit van Amsterdam, filed on Apr. 21, 2008, and the specification and claims thereof are incorporated herein by reference.

This application claims priority to and the benefit of the filing of Netherlands Patent Application Ser. No. 2000607, entitled "Manipulator for an Instrument for Minimally Invasive Surgery, and a Positioning Aid for Positioning Such an Instrument", filed on Apr. 24, 2007, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The invention relates to a manipulator for an instrument for minimally invasive surgery, having at a proximal end a handle for operating the instrument, and wherein the instrument is removably placed at a distal end, and wherein a parallelogram construction is provided between the proximal end and the distal end for guaranteeing an unambiguous positional relationship between the handle and the instrument.

2. Description of Related Art

Such a manipulator is known from the international patent application WO 03/086219.

SUMMARY DESCRIPTION OF THE INVENTION

It is an object of the invention to improve a manipulator in accordance with the preamble and thus to gain advantages that will become apparent hereinafter.

The manipulator according to the invention is characterized by one or several of the appended claims.

DETAILED DESCRIPTION OF THE INVENTION

In a first aspect of the invention, the manipulator is characterized in that the parallelogram construction is coupled with a system of bars for controlling the position of the parallelogram construction, the bars of the system of bars being connected to the parallelogram construction as well as to each other by means of cardan joints.

This achieves that during use, the manipulator according to the invention is subjected to little friction from the coupling interconnecting the bars of the system of bars and the parallelogram construction, allowing this manipulator to be operated with precision, and that during use of the manipulator, the user experiences adequate force feedback.

Advantageously, the system of bars is provided with at least one counterweight.

This affords the advantage of effectively compensating the weight of the parallelogram construction as well as of the relevant parts of the system of bars, which is desirable for adequately operating the manipulator.

Advantageously, the system of bars is provided with a counterweight that is incorporated in the bars of the system of bars.

This affords the advantage that the total weight, and as a consequence also the moment of inertia of the manipulator according to the invention, can be kept as low as possible. Instead of using a counterweight, it is also possible to provide the system of bars with compensating springs.

In still another aspect of the invention, the manipulator for an instrument for minimally invasive surgery that is provided with a handle at a proximal end, and an instrument at a distal end of the manipulator, and wherein a parallelogram construction is provided between the proximal end and the distal end for guaranteeing an unambiguous positional relationship between the handle and the instrument, is characterized in that the handle is coupled with an arm of the parallelogram construction via a cardan joint.

The use of such a cardan joint allows the manipulator to be operated with precision and accuracy because the movements of the handle can be transmitted to the instrument to be operated with precision.

To operate the instrument it is effective to use operating cables, which preferably pass through the cardan joint.

In order to guarantee the advantages gained by accurately operating the instrument by the handle, the manipulator according to the invention is preferably characterized in that each control cable is guided over a bypass wheel pertaining to that control cable, and having a rotation axis that coincides with a cardan shaft, and in that each bypass wheel co-operates with two support wheels provided at both sides of the bypass wheel and closely adjacent thereto, each of which is placed substantially at right angles to the bypass wheel and parallel to each other.

Hereinbefore the embodiment of the instrument has been left aside; the instrument may therefore be an integral part of the manipulator according to the invention or may be removable. With a view to ensuring that the instrument can be sterilized easily, this latter option is the usual embodiment.

In a further aspect of the invention, a manipulator for an instrument for minimally invasive surgery is provided, which is provided with a holder for such a removable instrument, wherein this instrument has operating flanges and the holder is equipped with spring clamps designed to co-operate with the operating flanges. In this way it is simple to repeatedly refit the instrument after sterilization.

Conceivably, the instrument may also be embodied as a disposable.

To allow the reusable or disposable instrument to be fitted simply and accurately, the invention also proposes a positioning aid that is provided with grooves, in which operating flanges of the instrument can be adjusted to a predetermined position, which grooves are also designed for co-operating with the spring clamps of the holder for the instrument, which holder is a part of the manipulator.

Hereinbefore, the embodiment of the holder has also been left aside; it may therefore be an integral part of the manipulator or may be removable therefrom. This latter option is preferred, because the holder is then easy to sterilize and may form a sterile barrier between the instrument and the non-sterile manipulator. Conceivably, the holder may also be embodied as disposable.

DESCRIPTION OF THE SEVERAL VIEWS OF THE DRAWINGS AND THE INVENTION

Hereinafter the invention will be further elucidated by way of an exemplary embodiment that does not limit the appended claims, and with reference to the drawing.

Figure 2:
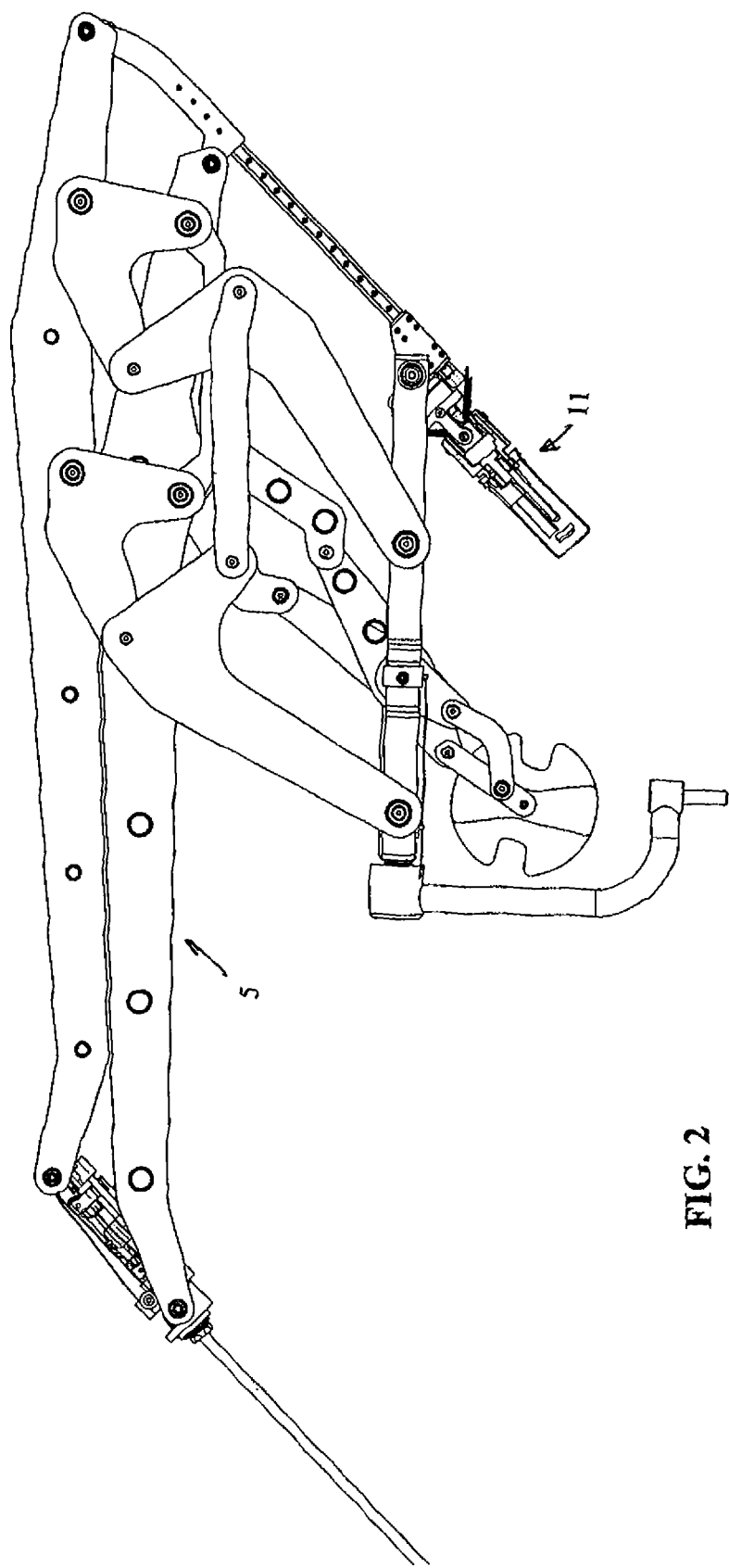
Figure 3:
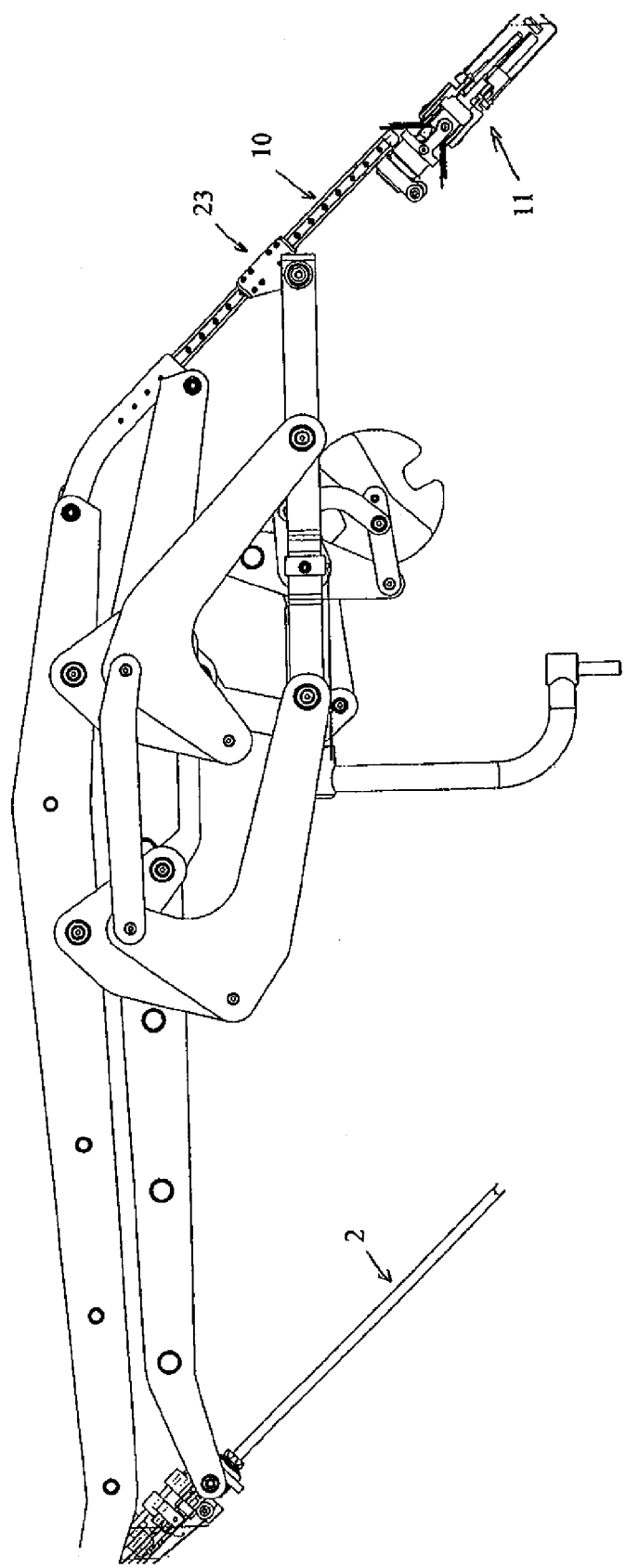
Figure 4:
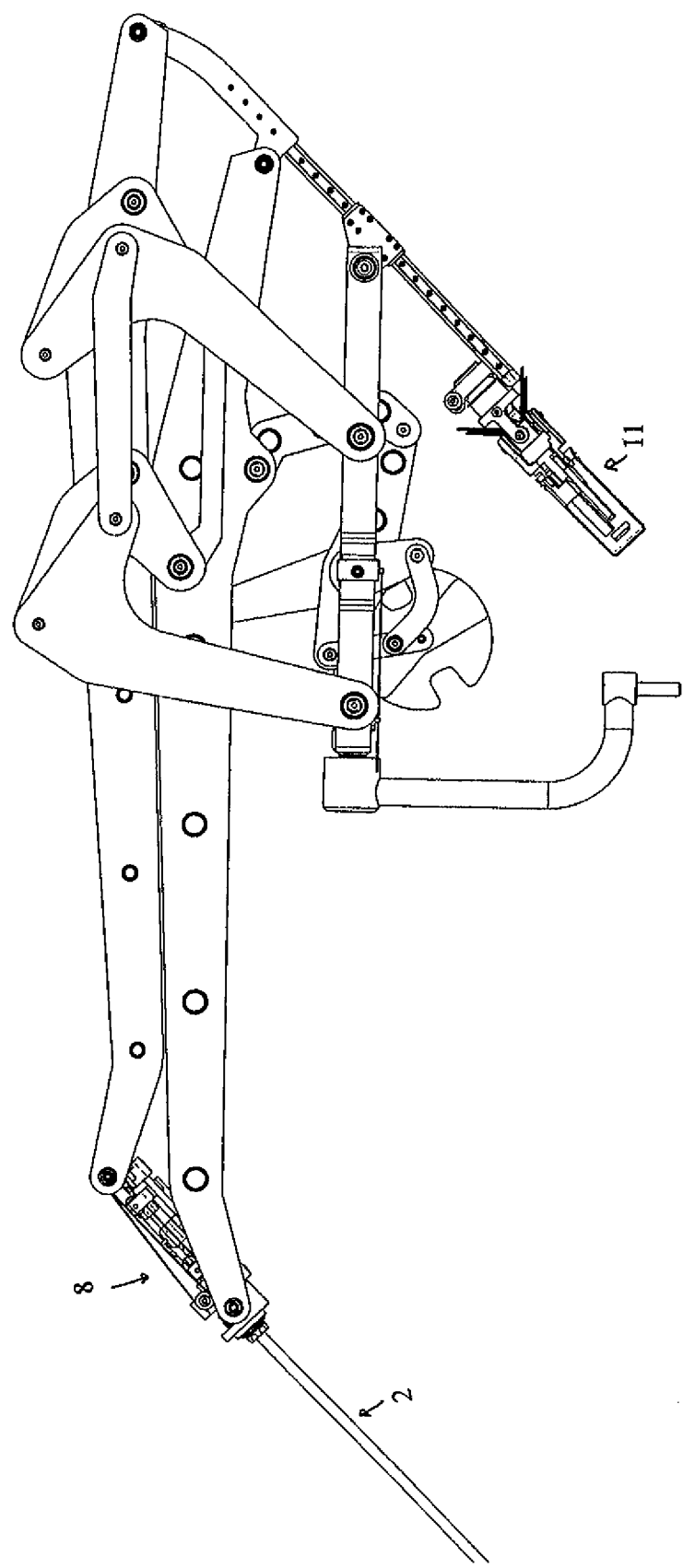
Figure 5:
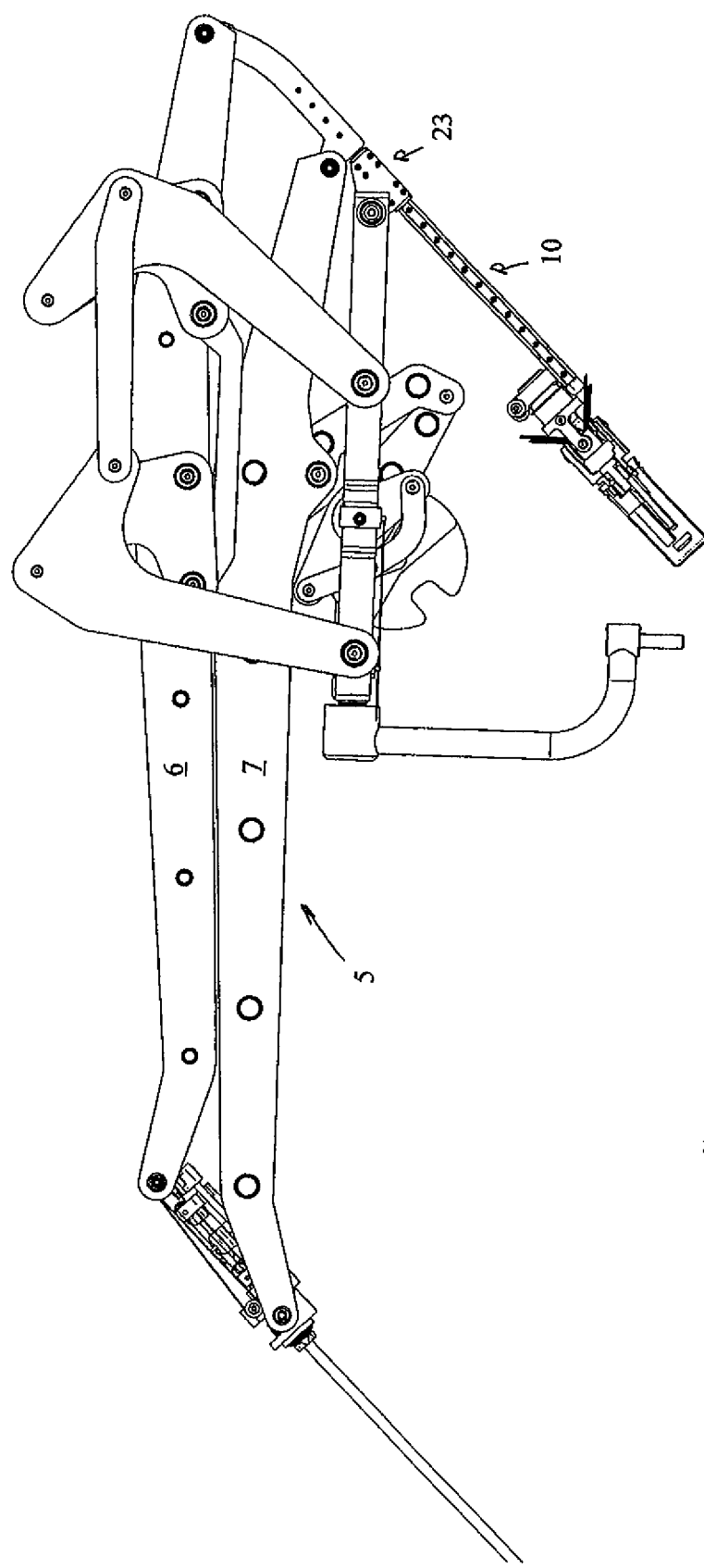
Figure 6:
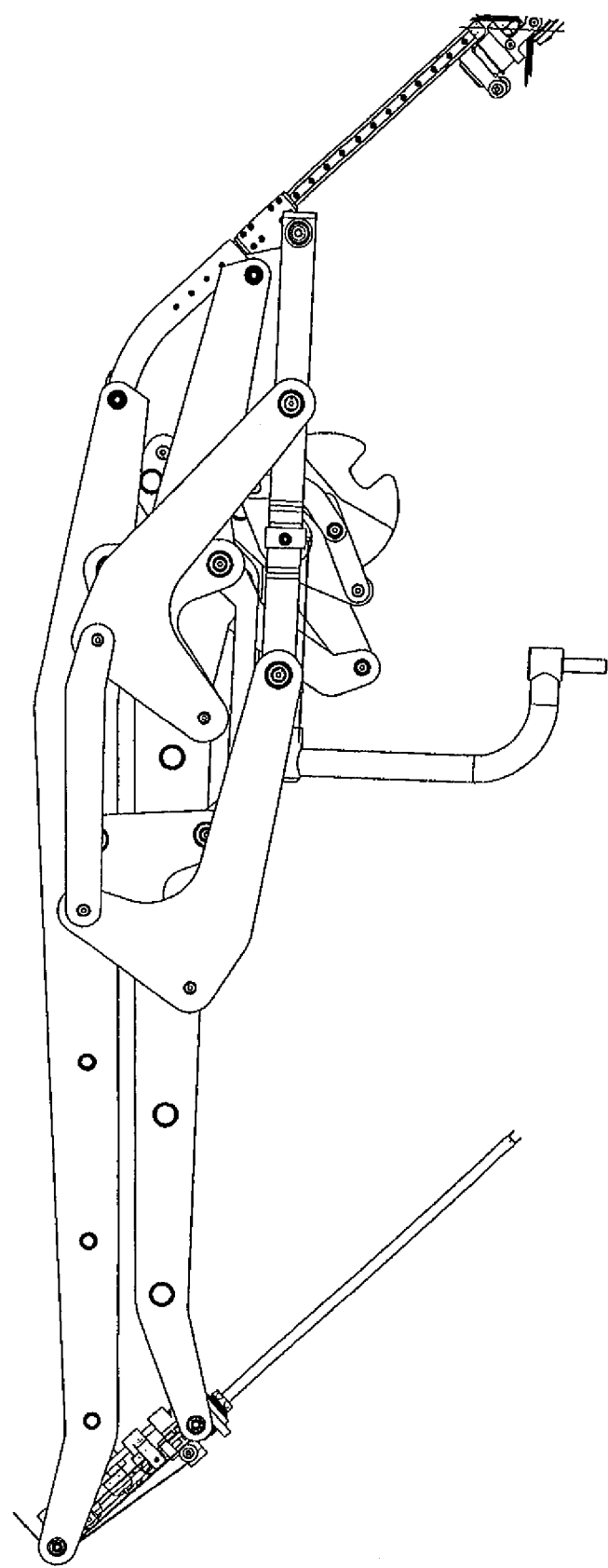
Figure 7:
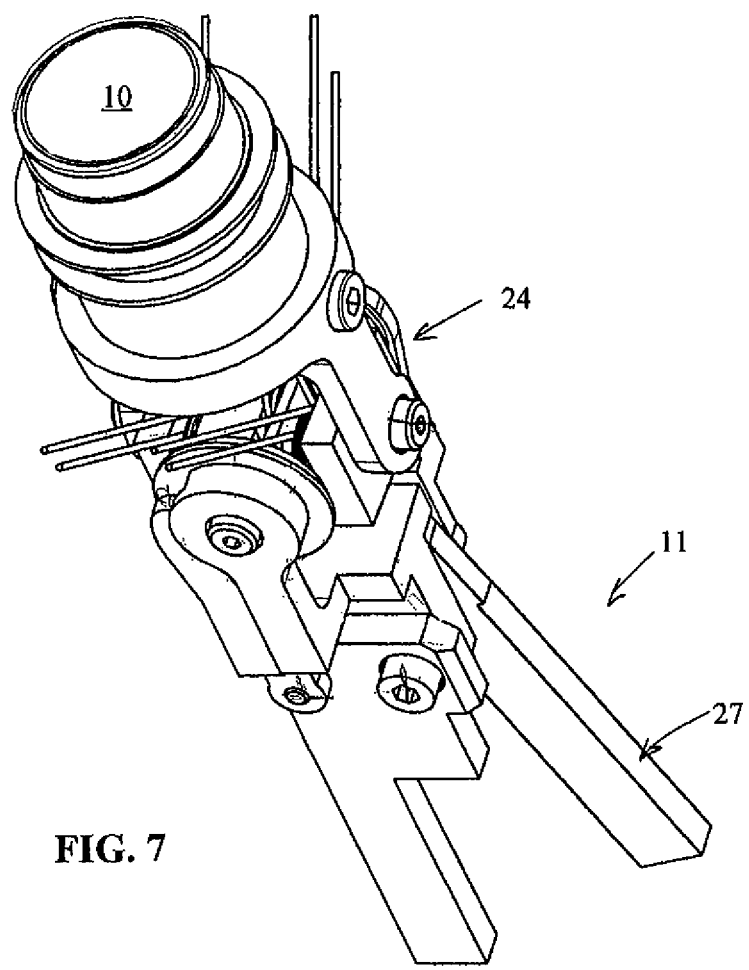
Figure 8:
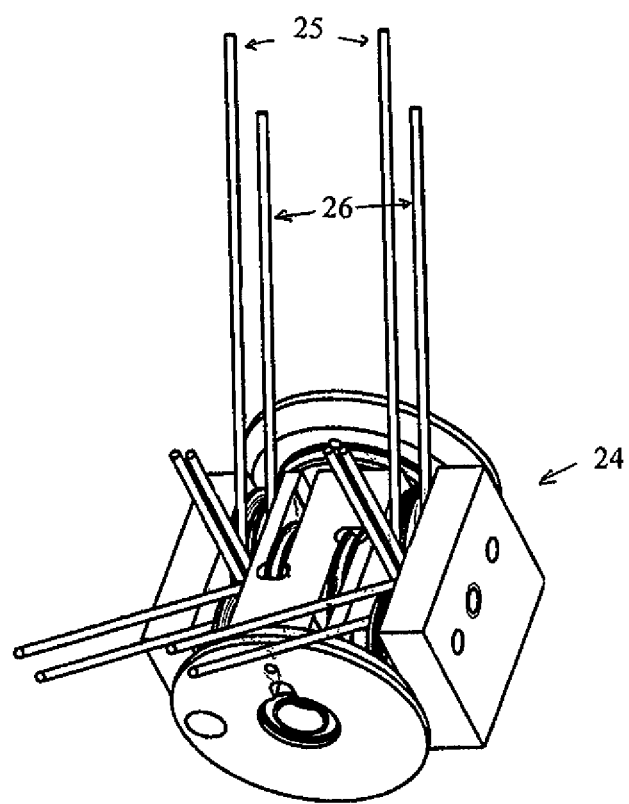
Figure 9:
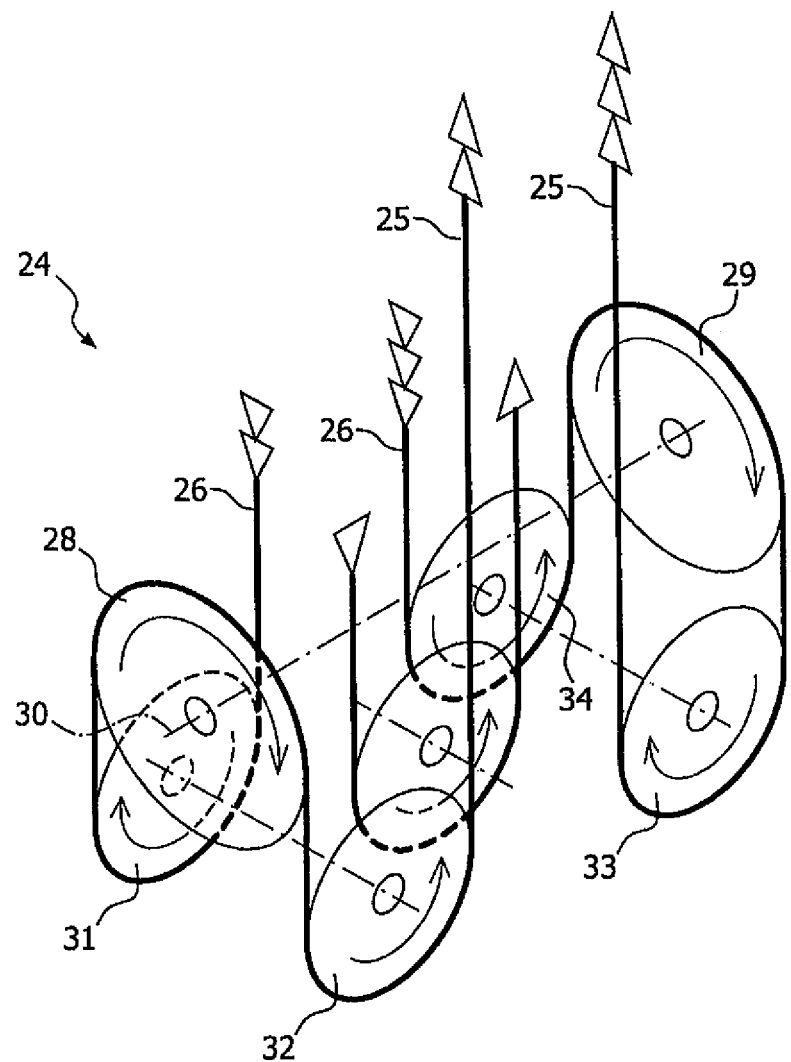
Figure 10:
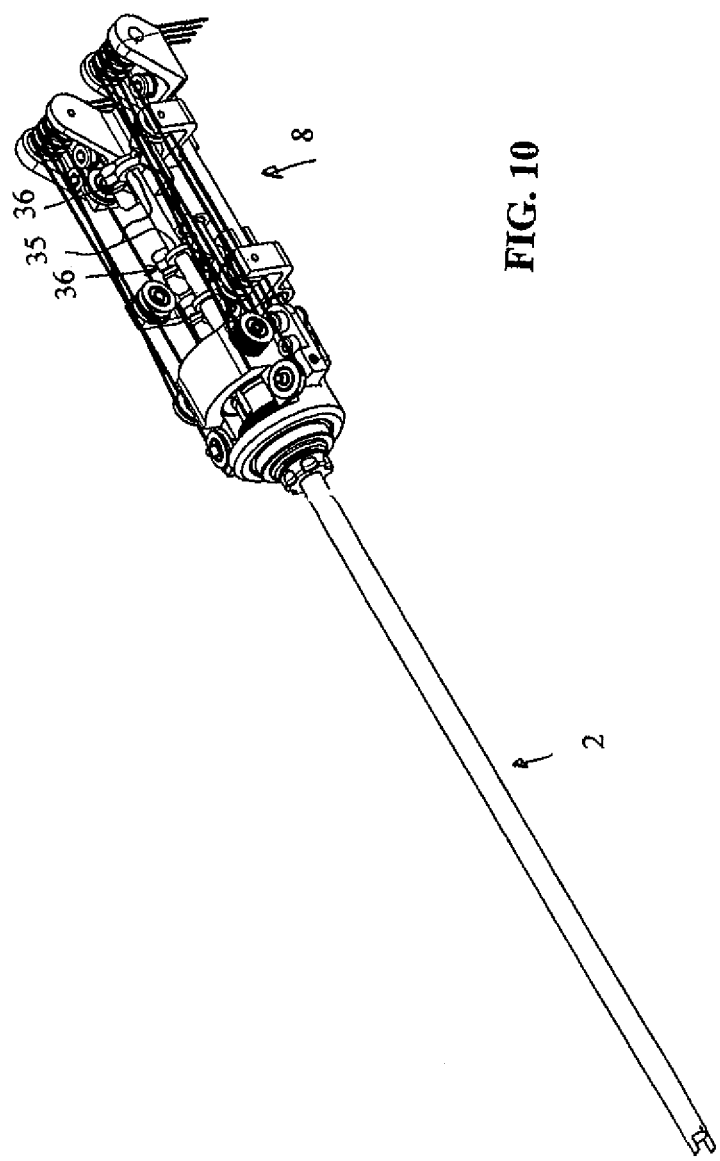
Figure 11:
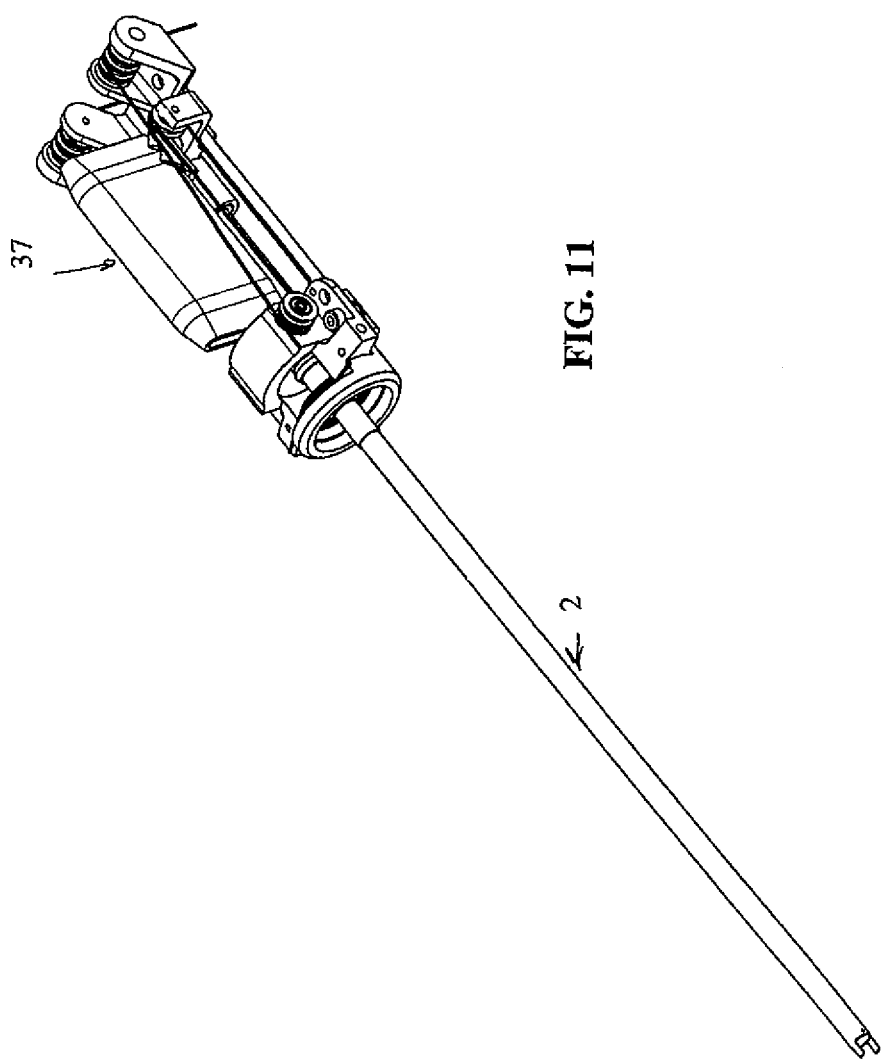

The drawing shows in:

FIG. 1 and FIG. 2 the manipulator according to the invention in a maximally raised position, in a neutral position, and in a position where it is moved to the right;

FIG. 3 and FIG. 4 the manipulator according to the invention in a position extended halfway upward and in a position where it is moved to the left and to the right, respectively;

FIG. 5 and FIG. 6, the manipulator according to the invention in a maximally downward position, in a position where it is moved to the right and to the left, respectively;

FIG. 7, the handle of the manipulator according to the invention in detail;

FIG. 8, a view of a cardan joint of the handle;

FIG. 9 a schematic representation of operating cables passing through the cardan joint of FIGS. 7 and 8;

FIG. 10 a detailed representation of the instrument fitted into a holder of the manipulator; and FIG. 11, the final stage of fitting an instrument into the holder of the manipulator, using a positioning aid.

Identical reference numerals in the figures refer to similar parts.

Referring first to FIG. 1, which shows a manipulator 1 for an instrument 2 that serves for minimally invasive surgery it can be seen that at a proximal end 3 a handle 11 is provided that serves for operating the instrument 2. This instrument 2 is located at a distal end 4 facing away from the proximal end 3. The instrument 2 can be removed from the manipulator 1 and replaced by a new or other instrument. The instrument is usually embodied as disposable.

FIG. 1 further shows that there is a parallelogram construction 5 between the proximal end 3 and the distal end 4. This parallelogram construction 5 has two substantially horizontally (parallel) extending arms 6 and 7, with the arms 6 and 7 being coupled with each other via a holder 8 for the instrument 2 at the distal end 4 of the manipulator 1, and by a vertically extending arm 9 having an elongated portion 10 ending at the proximal end 3 of the manipulator where the handle 11 is located. With this parallelogram construction 5 it is possible to guarantee an unambiguous positional relationship between the handle 11 and the instrument 2, so that the handle 11 and the instrument 2 maintain the same orientation.

In accordance with the invention, the parallelogram construction 5 is further coupled with a system of bars 12 for the positional control of the parallelogram construction 5, wherein the bars of the system of bars 12 are connected with the parallelogram construction 5 as well as with each other by means of cardan joints 13.

The system of bars 12 ensures that the position assumed by the horizontal arms 6 and 7, the holder 8 and the vertical arm 9 of the parallelogram construction 5 is unambiguously determined by the fact that the system of bars 12 is mounted on a horizontally extending main arm 14, which is in contact with solid ground.

On this main arm 14, two upwardly extending arm sections 15 and 16 are provided next to each other, interconnected via a coupling arm 17.

In turn, the arm sections 15 and 16 carry the operating arms 18 and 19, each of which is coupled with a horizontal arm 6 of the parallelogram construction 5 as well as being interconnected via the horizontally extending coupling arm 20. To compensate the weight of the parts to be moved by operating the handle 11, the system of bars 12 is further provided with a separate counterweight 21. The counterweight may, however, also be incorporated in the system of bars 12.

It will be obvious that bearings allow the main arm 14 to rotate around a support arm 22, which main arm 14 further has a fixed position, and that the guiding 23 for the elongated arm 10 coupled with the parallelogram construction 5 allows the manipulator 1 to be adjusted in height. The height is thus easily adjustable by operating the handle 11. The FIGS. 1 and 2 show the manipulator 1 in a position extended to maximum height, with FIG. 1 showing a neutral intermediate position, and FIG. 2 a position in which the handle 11 is moved to the left causing the parallelogram construction 5 to move to the right.

FIG. 3 shows the situation where the handle 11 is moved downward such that the elongated arm 10 is inserted halfway into the guiding 23. In this position the handle 11 has been moved to the right and the instrument 2 has undergone a corresponding movement.

FIG. 4 shows the position wherein the handle 11 has been moved to the left and the holder 8 for the instrument 2 has carried out a corresponding movement.

The FIGS. 5 and 6 likewise show a handle 11 that has been moved to the left or right, respectively, wherein the movements have been carried out with the parallelogram construction 5 in the lowest possible position. The guiding 23 is then at the top of the elongated arm 10 and immediately below the lower horizontal arm 7 of the parallelogram construction 5.

In FIG. 7 the handle 11 is represented as detail, showing also that the handle 11 has a cardan joint 24 connected with the elongated arm 10 that is coupled with the parallelogram construction 5.

FIG. 8 shows a detail of the cardan joint 24 in perspective, together with several operating cables 25 and 26 provided for operating the instrument 2 (see the FIGS. 1-6). By operating the handle 11, these operating cables 25 and 26 can be moved for a corresponding operation of actuator parts of the instrument 2. For example, if the instrument 2 is provided with grasping jaws that are pivotally mounted on the instrument 2, tilting the handle 11 in relation to the elongated arm 10 produces a corresponding movement of the pivoting grasping jaws of the instrument 2. Otherwise, operating the control organ 27 of the handle 11 {see FIG. 7) can produce a corresponding close or open movement of the grasping jaws. The way in which this may be accomplished is not new for the person skilled in the art, so that a further explanation by way of a figure description may be dispensed with.

Referring to FIG. 9, a further aspect of the invention will now be explained, relating to the construction of the cardan joint 24, and in particular to the way in which the operating cables 25, 26 move in this cardan joint 24.

While omitting several parts of the cardan joint that are irrelevant to the explanation, FIG. 9 shows the movement of the operating cables 25, 26 in the cardan joint 24.

FIG. 9 shows that each operating cable 25, 26 is guided over a bypass wheel 28, 29 pertaining to that operating cable 25, 26, and possessing a rotational axis 30 that coincides with a cardan shaft of the cardan joint 24.

Each bypass wheel 28, 29 is further shown to co-operate with two support wheels provided at both sides of the bypass wheel 28, 29 and very closely adjacent thereto.

With regard to the bypass wheel 28, this concerns the support wheels 31 and 32, and with regard to the bypass wheel 29 it concerns the support wheels 33 and 34.

FIG. 9 shows that each of the support wheels 31, 32, 33 and 34 are placed at right angles in relation to the respective bypass wheel 28, 29 as well as parallel to each other.

Still another aspect of the invention will be further explained with reference to the FIGS. 10 and 11.

This relates to the aspect of the invention that the manipulator for an instrument for minimally invasive surgery, wherein the instrument is accommodated in a holder 8, for example disposable instrument 2, and wherein the instrument 2 comprises operating flanges 35 and the holder 8 is provided with spring clamps 36 designed to co-operate with these operating flanges 35. The manner of operating the instrument 2 with these operating flanges 35 is explained in the above-mentioned international patent application WO 03/086219, the contents of which are herewith deemed to be inserted and incorporated in their entirety.

To allow the instrument 2 to be placed with precision and accuracy, a further aspect of the invention proposes a positioning aid 37, shown in FIG. 11.

This positioning aid 37 for placing an instrument 2 for minimally invasive surgery into a manipulator 1 for such an instrument is provided with grooves for receiving the operating flanges 35 of the instrument 2 shown in FIG. 10, so that these flanges 35 can be adjusted to a predetermined position that corresponds to a completely extended and closed position of the instrument 2, such that the instrument 2 can be placed accurately into the holder 8, and the flanges 35 can be placed accurately into the spring clamps 36 of the holder 8.

The afore-mentioned grooves of the positioning aid 37 are also useful for conveniently running said flanges in the spring clamps 36 of the holder 8 for the instrument 2.

The above specification describes and explains some aspects of the manipulator according to the invention, attention being drawn to the fact that these aspects may also be applied singly and with equal effect.

The above description and explanation must therefore be understood to serve solely as elucidation of the appended claims without necessarily limiting these to the specific exemplary embodiment given. The protective scope due the invention is therefore determined exclusively by the appended claims, which should be interpreted in the broadest sense as the embodiment of that which in realizing the manipulator according to the invention is felt by the inventors to be the true essence. Any variations that may be anticipated or may be developed only afterwards and that fulfill the essence of the invention revealed in the description given above therefore fall in full under the appended claims.

What is claimed is:

1. A manipulator for an instrument for minimally invasive surgery, having at a proximal end a handle for operating the instrument, and wherein the instrument is removably placed at a distal end, and wherein a parallelogram construction is provided between the proximal end and the distal end for guaranteeing an unambiguous positional relationship between the handle and the instrument, and wherein the parallelogram construction is coupled with a system of bars for controlling the position of the parallelogram construction, the bars of the system of bars being connected to the parallelogram construction as well as to each other by means of cardan joints, said system of bars being mounted on a horizontally extending main arm, and wherein on this main arm two next to each other upwardly extending arm sections are provided that are interconnected via a first coupling arm, which arm sections carry operating arms that are coupled with a horizontal arm of the parallelogram constructions as well as being mutually interconnected via a second, horizontally extending, coupling arm.

2. A manipulator according to claim 1, wherein the system of bars is provided with at least one counterweight and/or compensating springs.

3. A manipulator according to claim 1, wherein the system of bars is provided with a counterweight that is incorporated in the bars of the system of bars.

4. A manipulator according to claim 1, wherein the handle is coupled with an arm of the parallelogram construction via a cardan joint.

5. A manipulator according to claim 4, additionally comprising control cables that pass through the cardan joint and are in operable communication with the handle.

6. A manipulator according to claim 5, wherein each control cable is guided over a bypass wheel pertaining to that control cable and has a rotation axis that coincides with a cardan shaft, and wherein each bypass wheel co-operates with two support wheels provided at opposing sides of the bypass wheel and closely adjacent thereto, each of which is placed substantially at right angles to the bypass wheel and parallel to each other.

\* \* \* \* \*